(12) United States Patent
Epstein et al.

(10) Patent No.: US 10,945,746 B2
(45) Date of Patent: Mar. 16, 2021

(54) TOOLS FOR SHEATHING TREATMENT DEVICES AND ASSOCIATED SYSTEMS AND METHODS

(71) Applicant: Covidien LP, Mansfield, MA (US)

(72) Inventors: Evan David Epstein, Costa Mesa, CA (US); Joseph Marrocco, Costa Mesa, CA (US); David G. Matsuura, Del Mar, CA (US); Philip J. Simpson, Escondido, CA (US); Jeffrey J. Loos, Carlsbad, CA (US); Adam Hattan, Long Beach, CA (US)

(73) Assignee: COVIDIEN LP, Mansfield, MA (US)

( * ) Notice: Subject to any disclaimer, the term of this patent is extended or adjusted under 35 U.S.C. 154(b) by 362 days.

(21) Appl. No.: 16/007,961

(22) Filed: Jun. 13, 2018

(65) Prior Publication Data

US 2018/0353196 A1 Dec. 13, 2018

Related U.S. Application Data

(60) Provisional application No. 62/518,586, filed on Jun. 12, 2017.

(51) Int. Cl.
*A61F 2/82* (2013.01)
*A61B 17/221* (2006.01)
(Continued)

(52) U.S. Cl.
CPC ....... *A61B 17/221* (2013.01); *A61M 25/0194* (2013.01); *A61B 2017/0053* (2013.01);
(Continued)

(58) Field of Classification Search
CPC .......... A61B 17/221; A61B 2017/0053; A61B 2017/2215; A61M 25/0194;
(Continued)

(56) References Cited

U.S. PATENT DOCUMENTS 2,918,919 A 12/1959 Wallace
2,943,626 A 7/1960 Dormia
(Continued)

FOREIGN PATENT DOCUMENTS

CN 1640505 A 7/2005
CN 102036611 A 4/2011
(Continued)

*Primary Examiner* — Erich G Herbermann
(74) *Attorney, Agent, or Firm* — Fortem IP LLP; Mary Fox

(57) ABSTRACT

Devices for loading intravascular treatment devices into a sheath and associated systems and methods are disclosed herein. A sheathing tool may include, for example, a first channel extending to a first opening, the first channel configured to receive a treatment device in a constrained state therethrough. The treatment device may include an elongated member and a first element and a second element at a distal region of the elongated member. The second channel may extend to a second opening, the second opening surrounded by a sidewall and configured to receive the treatment device in the constrained state therethrough, wherein the second opening is spaced apart from the first opening by a gap, and wherein a length of the gap is great enough to allow the first element to self-expand over the sidewall while the second element generally maintains its diameter in the constrained state while crossing the gap.

15 Claims, 14 Drawing Sheets

(51) Int. Cl.
*A61M 25/01* (2006.01)
*A61F 2/962* (2013.01)
*A61M 25/00* (2006.01)
*A61M 25/06* (2006.01)
*A61B 17/00* (2006.01)

(52) U.S. Cl.
CPC ....... *A61B 2017/2215* (2013.01); *A61F 2/962* (2013.01); *A61M 2025/0034* (2013.01); *A61M 2025/0681* (2013.01)

(58) Field of Classification Search
CPC ... A61M 2025/0034; A61M 2025/0681; A61F 2/962; A61F 2/95; A61F 2/94; A61F 2/9517; A61F 2/9522; A61F 2/82; A61F 2/24; A61F 2002/9505
See application file for complete search history.

(56) References Cited

U.S. PATENT DOCUMENTS

| | | |
|---|---|---|
| 3,996,938 A | 12/1976 | Clark, III |
| 4,347,646 A | 9/1982 | Dormia |
| 4,611,594 A | 9/1986 | Grayhack et al. |
| 4,650,466 A | 3/1987 | Luther |
| 4,657,020 A | 4/1987 | Lifton |
| 4,699,147 A | 10/1987 | Chilson et al. |
| 4,790,812 A | 12/1988 | Hawkins, Jr. et al. |
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach, Jr. et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,911,710 A * | 6/1999 | Barry ............... A61M 39/0693 604/167.04 |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,984,957 A | 11/1999 | Laptewicz, Jr. et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |

(56) References Cited

U.S. PATENT DOCUMENTS

| | | |
|---|---|---|
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,399,308 B2 | 7/2008 | Borillo et al. |
| 7,534,252 B2 | 5/2009 | Sepetka et al. |
| 7,578,830 B2 | 8/2009 | Kusleika et al. |
| 7,621,870 B2 | 11/2009 | Berrada et al. |
| 7,837,702 B2 | 11/2010 | Bates |
| 8,070,791 B2 | 12/2011 | Ferrera et al. |
| 8,088,140 B2 | 1/2012 | Ferrera et al. |
| 8,105,333 B2 | 1/2012 | Sepetka et al. |
| 8,197,493 B2 | 6/2012 | Ferrera et al. |
| 8,603,014 B2 | 12/2013 | Alleman et al. |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0041909 A1 | 11/2001 | Tsugita et al. |
| 2001/0044632 A1 | 11/2001 | Daniel et al. |
| 2001/0044634 A1 | 11/2001 | Don Michael et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0138094 A1 | 9/2002 | Borillo et al. |
| 2002/0151928 A1 | 10/2002 | Leslie et al. |
| 2002/0169474 A1 | 11/2002 | Kusleika et al. |
| 2002/0188314 A1 | 12/2002 | Anderson et al. |
| 2002/0193825 A1 | 12/2002 | McGuckin et al. |
| 2003/0004542 A1 | 1/2003 | Wensel et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0144687 A1 | 7/2003 | Brady et al. |
| 2003/0153935 A1 | 8/2003 | Mialhe |
| 2003/0176884 A1 | 9/2003 | Berrada et al. |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0133232 A1 | 7/2004 | Rosenbluth et al. |
| 2004/0138692 A1 | 7/2004 | Phung et al. |
| 2004/0153025 A1 | 8/2004 | Seifert et al. |
| 2004/0153118 A1 | 8/2004 | Clubb et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1 | 3/2005 | Sepetka et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0125024 A1 | 6/2005 | Sepetka et al. |
| 2005/0131450 A1 | 6/2005 | Nicholson et al. |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1 | 9/2005 | Sepetka et al. |
| 2005/0234501 A1 | 10/2005 | Barone |
| 2005/0234505 A1 | 10/2005 | Diaz et al. |
| 2005/0277978 A1 | 12/2005 | Greenhalgh |
| 2005/0283166 A1 | 12/2005 | Greenhalgh |
| 2005/0283186 A1 | 12/2005 | Berrada et al. |
| 2006/0004404 A1 | 1/2006 | Khachin et al. |
| 2006/0009784 A1 | 1/2006 | Behl et al. |
| 2006/0030925 A1 | 2/2006 | Pryor |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0271153 A1 | 11/2006 | Garcia et al. |
| 2006/0276805 A1 | 12/2006 | Yu |
| 2006/0282111 A1 | 12/2006 | Morsi |
| 2006/0287668 A1 | 12/2006 | Fawzi et al. |
| 2007/0112374 A1 | 5/2007 | Paul et al. |
| 2007/0116165 A1 | 5/2007 | DeMello et al. |
| 2007/0149996 A1 | 6/2007 | Coughlin |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0198051 A1 | 8/2007 | Clubb et al. |
| 2007/0225749 A1 | 9/2007 | Martin et al. |
| 2007/0233236 A1 | 10/2007 | Pryor |
| 2007/0265656 A1 | 11/2007 | Amplatz et al. |
| 2008/0109031 A1 | 5/2008 | Sepetka et al. |
| 2008/0183198 A1 | 7/2008 | Sepetka et al. |
| 2008/0188885 A1 | 8/2008 | Sepetka et al. |
| 2008/0262528 A1 | 10/2008 | Martin |
| 2008/0262532 A1 | 10/2008 | Martin |
| 2009/0069828 A1 | 3/2009 | Martin et al. |
| 2009/0105722 A1 | 4/2009 | Fulkerson et al. |
| 2009/0105737 A1 | 4/2009 | Fulkerson et al. |

(56) References Cited

U.S. PATENT DOCUMENTS

| | | |
|---|---|---|
| 2009/0125053 A1 | 5/2009 | Ferrera et al. |
| 2009/0192518 A1 | 7/2009 | Golden et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Fulkerson et al. |
| 2010/0256600 A1 | 10/2010 | Ferrera |
| 2010/0318097 A1 | 12/2010 | Ferrera et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |
| 2013/0030461 A1 | 1/2013 | Marks et al. |
| 2013/0281788 A1 | 10/2013 | Garrison |
| 2014/0276074 A1 | 9/2014 | Warner |
| 2014/0343595 A1 | 11/2014 | Monstadt et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0354098 A1 | 12/2016 | Martin et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| DE | 3501707 A1 | 7/1986 |
| EP | 200668 A2 | 11/1986 |
| EP | 1312314 A1 | 5/2003 |
| EP | 2319575 B1 | 11/2013 |
| JP | 2002537943 A | 11/2002 |
| JP | 2007-522881 A | 8/2007 |
| JP | 2007252951 A | 10/2007 |
| JP | 2011508635 | 3/2011 |
| JP | 2014004219 A | 1/2014 |
| JP | 2018118132 A | 8/2018 |
| KR | 20180102877 A | 9/2018 |
| WO | WO-94/09845 A1 | 5/1994 |
| WO | WO-95/09586 A1 | 4/1995 |
| WO | WO-9601591 A1 | 1/1996 |
| WO | WO-96/17634 A2 | 6/1996 |
| WO | WO-96/19941 A1 | 7/1996 |
| WO | WO-97/27808 A1 | 8/1997 |
| WO | WO-97/27893 A1 | 8/1997 |
| WO | WO-98/03120 A1 | 1/1998 |
| WO | WO-00/53120 A1 | 9/2000 |
| WO | WO-0072909 A1 | 12/2000 |
| WO | WO-01/32254 A1 | 5/2001 |
| WO | WO-01/54622 A1 | 8/2001 |
| WO | WO-01/67967 A1 | 9/2001 |
| WO | WO-02/02162 | 1/2002 |
| WO | WO-02/28291 A2 | 4/2002 |
| WO | WO-03/000334 A1 | 1/2003 |
| WO | WO-03/061730 A2 | 10/2003 |
| WO | WO-03/089039 A | 10/2003 |
| WO | WO-2006/031410 A2 | 3/2006 |
| WO | WO-2006/122076 A1 | 11/2006 |
| WO | WO-2007092820 A2 | 8/2007 |
| WO | WO-2008/036156 A1 | 3/2008 |
| WO | WO-2008036156 | 3/2008 |
| WO | WO-2008/131116 A1 | 10/2008 |
| WO | 2008539958 A | 11/2008 |
| WO | WO-2009/034456 A2 | 3/2009 |
| WO | WO-2009/086482 A1 | 7/2009 |
| WO | WO-2011/092383 A1 | 7/2011 |
| WO | WO-2011091383 | 7/2011 |
| WO | WO-2012009675 A2 | 1/2012 |
| WO | WO-2012/162437 A1 | 11/2012 |
| WO | WO-2013/106146 A1 | 7/2013 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

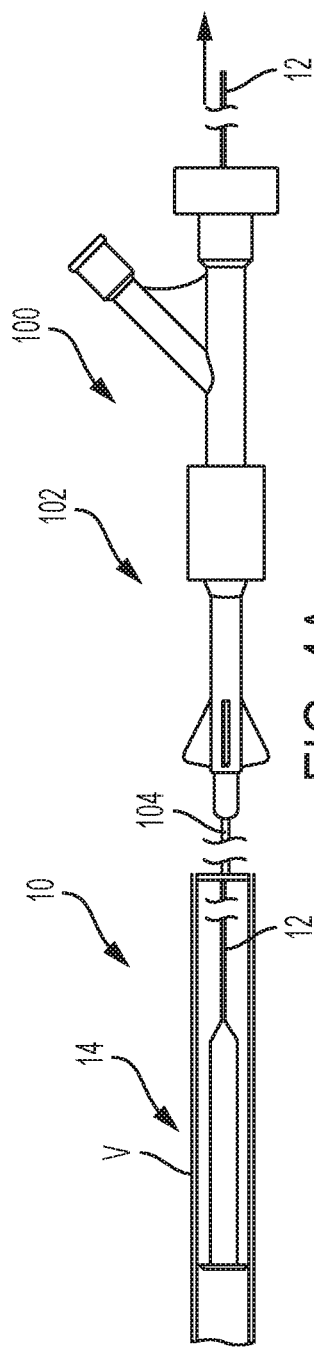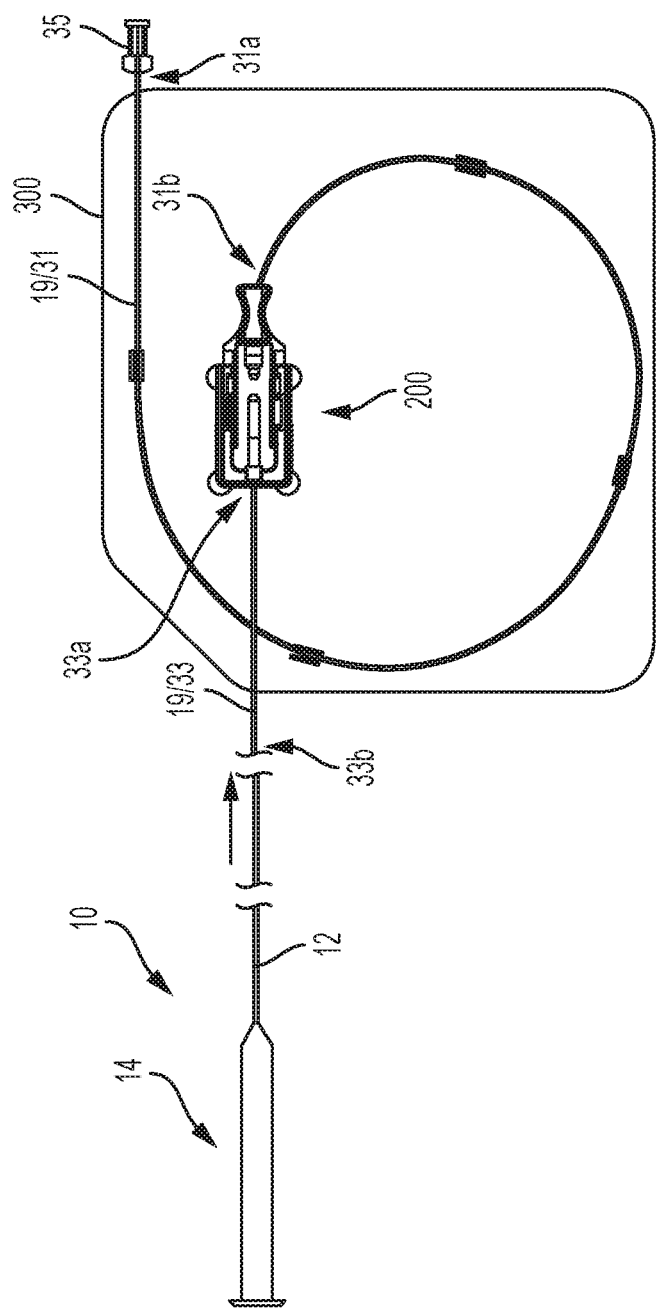

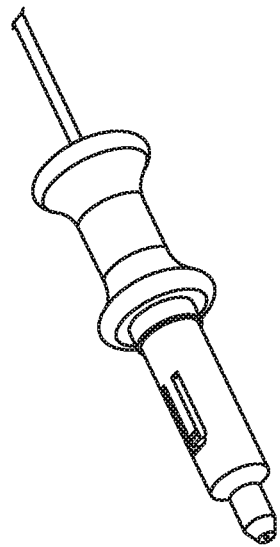
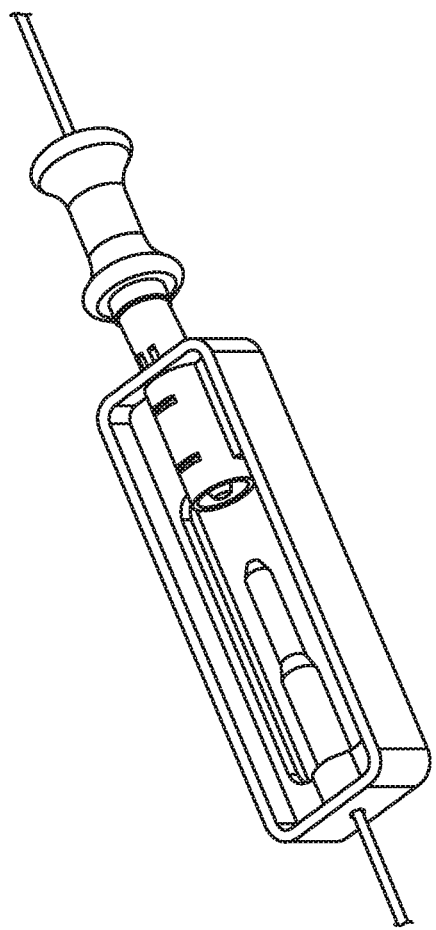
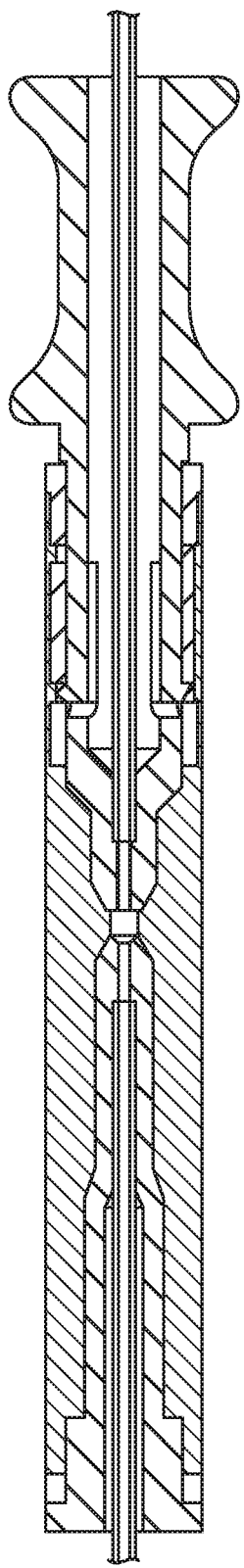
FIG. 8A
FIG. 8C
FIG. 8B

TOOLS FOR SHEATHING TREATMENT DEVICES AND ASSOCIATED SYSTEMS AND METHODS

TECHNICAL FIELD

The present technology relates generally to sheathing tools and associated systems and methods. Some embodiments of the present technology relate to devices for loading an intravascular treatment device into a sheath.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Even in successful procedures, a physician must be cautious to prevent the walls of the vessel or body lumen from imparting undesired forces to shear or dislodge the obstruction as it passes through the vasculature during removal. These forces have the potential of fragmenting the obstruction. In some cases, the obstruction can simply break free from the retrieval device and can lodge in a new area causing more concern than the original blockage.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death (infarction). Accordingly, it is desirable to provide immediate medical treatment of an ischemic stroke. To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages using this approach.

For example, one disadvantage is that the stent may not sufficiently retain the clot as it pulls the clot to the catheter. In such a case, some or all of the clot might remain the vasculature. Another risk is that as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter. Regardless, simply dragging an expanded stent (either fully or partially expanded) can result in undesired trauma to the vessel. In most cases, since the stent is oversized compared to the vessel, dragging a fixed metallic (or other) structure can pull the arteries and/or strip the cellular lining from the vessel, causing further trauma such as a hemorrhagic stroke (leakage of blood from a cerebral vessel). Also, the stent can become lodged on plaque on the vessel walls resulting in further vascular damage.

In view of the above, there remains a need for improved devices and methods that can remove occlusions from body lumens and/or vessels.

SUMMARY

At least some of the embodiments disclosed herein are devices, systems, and methods for facilitating a user in positioning an expandable, intravascular treatment device within a lumen of a catheter and/or sheath. For example, certain medical procedures may require multiple passes of the same treatment device in order to effectively treat the patient. Between passes, the treatment device is often completely removed from the catheter and/or patient and must be re-loaded into the catheter for the next pass. For instance, removing clot material from a blood vessel of a patient may include advancing a clot retrieving device to a treatment site within the blood vessel lumen, capturing at least a portion of the clot material with the clot retrieving device, removing the clot material and clot retrieving device from the patient, then repeating the foregoing process until a sufficient amount of clot material is removed.

Some embodiments of the present technology include a device for sheathing (and/or re-sheathing) a treatment device, such as a clot retrieving device. In some embodiments, the device includes a first channel and a second channel, each of which are configured to receive the treatment device in a constrained state therethrough. In some embodiments, the first channel may extend to a first opening and the second channel may extend to a second opening that is surrounded by a sidewall. The second opening may be spaced apart from the first opening by a gap, and the length of the gap may be great enough to allow a first portion of the treatment device to self-expand over the sidewall while a second portion of the treatment device generally maintains its diameter in the constrained state while crossing the gap.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause (1, 16, 20, 23, etc.). The other clauses can be presented in a similar manner.

1. A device for sheathing a treatment device having an elongated member and a first element and a second element at a distal region of the elongated member, wherein the device comprises:
    a first channel extending to a first opening, the first channel configured to receive the treatment device in a constrained state therethrough; and
    a second channel extending to a second opening, the second opening surrounded by a sidewall and configured to receive the treatment device in the constrained state therethrough, wherein the second opening is spaced apart from the first opening by a gap, and wherein a length of the gap is great enough to allow the first element to self-expand over the sidewall while the second element generally maintains its diameter in the constrained state while crossing the gap.
2. The device of Clause 1, wherein an inner diameter of the second channel tapers distally from the second opening.
3. The device of Clause 1 or Clause 2, wherein an outer diameter of the sidewall increases distally from the second opening.
4. The device of any one of Clauses 1-3, wherein the first and second openings are fixed relative to one another such that the length of the gap is fixed.
5. The device of any one of Clauses 1-4, wherein the first and second openings are movable relative to one another such that the length of the gap is adjustable.
6. The device of any one of Clauses 1-5, wherein the first channel is within a first housing and the second channel is within a second housing movable relative to the first housing, and wherein the first housing has a detent configured to receive a protrusion of the second housing, or vice versa, such that the first housing is locked in place relative to the second housing.
7. The device of any one of Clauses 1-6, wherein the first channel is configured to receive a sheath therethrough, wherein the sheath is configured to slidably receive the treatment device therein in the constrained state.
8. The device of any one of Clauses 1-7, wherein the second channel is configured to receive a sheath therethrough, and wherein the sheath is configured to slidably receive the treatment device therein in the constrained state.
9. The device of any one of Clauses 1-8, wherein the first element is a self-expanding element.
10. The device of any one of Clauses 1-9, wherein the second element is a self-expanding element.
11. The device of any one of Clauses 1-10, wherein the first element is a mesh.
12. The device of any one of Clauses 1-11, wherein the second element is a stent.
13. The device of any one of Clauses 1-12, wherein, in an expanded state, the first element has a flared distal region with a lumen therethrough, and wherein the lumen of the flared distal region is configured to receive the sidewall therein as the treatment device is moved through the across the gap.
14. The device of any one of Clauses 1-13, wherein the treatment device is a clot retrieving device.
15. The device of any one of Clauses 1-14, wherein the device is configured to be detachably coupled to a handle of a catheter, thereby placing the second channel in fluid communication with a lumen of the catheter.
16. A system for sheathing a treatment device having an elongated member and a first element and a second element at a distal region of the elongated member, wherein the device comprises:
    a sheath configured to receive the treatment device in a constrained state therethrough;
    a first channel extending to a first opening and configured to receive at least a portion of the sheath; and
    a second channel extending to a second opening, the second opening surrounded by a sidewall and configured to receive the treatment device in the constrained state therethrough, wherein the second opening is spaced apart from the first opening by a gap, and wherein a length of the gap is great enough to allow the first element to self-expand over the sidewall while the second element generally maintains its diameter in the constrained state while crossing the gap.
17. The system of Clause 16, further comprising a fluid port coupled to a proximal end portion of the sheath.
18. The system of Clause 16 or Clause 17, wherein the sheath is a first sheath and the system further comprises a second sheath configured to receive the treatment device in a constrained state therethrough, and wherein the second channel is configured to receive at least a portion of the second sheath therein.
19. The system of Clause 18, further comprising a catheter, and wherein the second sheath is configured to be coupled to the catheter.
20. A system for sheathing a treatment device having an elongated member and a first element and a second element at a distal region of the elongated member, wherein the device comprises:
    a sheath configured to receive the treatment device in a constrained state therethrough;
    a sheathing tool comprising:
        a first channel extending to a first opening and configured to receive at least a portion of the sheath, and
        a second channel extending to a second opening, the second opening surrounded by a sidewall and configured to receive the treatment device in the constrained state therethrough, wherein the second opening is spaced apart from the first opening by a gap, and wherein a length of the gap is great enough to allow the first element to self-expand over the sidewall while the second element generally maintains its diameter in the constrained state while crossing the gap;
    a housing configured to be detachably coupled to the sheath and the sheathing tool, wherein a majority of the length of the sheath is contained within a perimeter of the housing such that a user may position manipulate both ends of the sheath and/or treatment device without taking a step.
21. The system of Clause 20, wherein the sheath is a first sheath and the system further comprises a second sheath configured to receive the treatment device in a constrained state therethrough, and wherein the second channel is configured to receive at least a portion of the second sheath therein.
22. The system of Clause 21, further comprising a catheter, and wherein the second sheath is configured to be coupled to the catheter.
23. A method for sheathing a treatment device having an elongated member and a first element and a second element at a distal region of the elongated member, the method comprising:
   positioning the treatment device in a first channel with the first and second elements in a constrained state;
   moving the treatment device from a first opening of the first channel through a second opening of a second channel spaced apart from the first opening by a gap; and
   while moving the treatment device across the gap, generally maintaining a cross-sectional dimension of the first element at its cross-sectional dimension in the constrained state while allowing the second element to expand over a sidewall surrounding the second opening.
24. The method of Clause 23, further comprising moving a portion of the second element in a first direction through the second channel while moving a second portion of the second element in a second direction opposite the first direction outside of the channel.
25. The method of Clause 23 or Clause 24, further comprising moving the treatment device along the first channel in a first direction, and wherein moving the treatment device from the first opening and through the second opening is in a second direction opposite the first direction.
26. The method of any one of Clauses 23-25, wherein moving the treatment device from the first opening and through the second opening in the second direction occurs after moving the treatment device along the first channel in the first direction.
27. The method of any one of Clauses 23-26, further comprising moving the treatment device along the second channel in a first direction, and wherein moving the treatment device from the first opening and through the second opening is in a second direction opposite the first direction.
28. The method of Clause 27, wherein moving the treatment device from the first opening and through the second opening in the second direction occurs after moving the treatment device along the second channel in the first direction.
29. The method of any one of Clauses 23-28, wherein the constrained state is a first constrained state and the treatment device is movable to a second constrained state in which the second element is inverted relative to its position when the treatment device is in a first constrained state.
30. The method of Clause 29, further comprising inverting the second element by moving the first element through the second channel while the second element surrounds the sidewall.
31. The method of Clause 29 or Clause 30, further comprising moving the treatment device in the second constrained state through the second channel.
32. The method of any one of Clauses 29-31, further comprising moving the treatment device in the second constrained state through the second channel and into a catheter.
33. The method of any one of Clauses 23-32, further comprising decreasing a length of the gap before moving the treatment device through the first opening.
34. The method of any one of Clauses 23-33, further comprising decreasing a length of the gap after moving the treatment device across a portion of the gap.
35. The method of any one of Clauses 23-34, further comprising removing the treatment device from a catheter before positioning the first and second elements in the first channel.
36. The method of Clause 35, further comprising removing clot material from the treatment device before positioning the first and second elements in the first channel.
37 The method of Clause 36, wherein removing clot material includes rinsing clot material from the treatment device.
38. The method of Clause 35, further comprising removing clot material from the treatment device while at least a portion of the elongated member is positioned within the first channel but before positioning the first and second elements in the first channel.
39. The method of Clause 38, wherein removing clot material includes rinsing clot material from the treatment device.
40. A device for transferring an intravascular treatment device from a first sheath to a second sheath, the treatment device including first and second self-expanding elements, wherein each of the first and second sheaths is sized such that the treatment device is constrained in a compressed state when positioned within each of the first and second sheaths, and wherein the device comprises:
   a first channel configured to receive at least a portion of the first sheath therein, the first channel having a first proximal opening configured to receive the first sheath therethrough and a first distal opening; and
   a second channel configured to receive at least a portion of the second sheath therein, the second channel having a second proximal opening and a second distal opening configured to receive the second sheath therethrough,
   wherein the device is configured to securely position the first and second channels relative to one another such that the first distal opening is aligned with the second proximal opening and spaced apart from the second proximal opening by a gap, the gap having a length such that, when the first and second sheaths are positioned within the first and second channels, respectively, and the treatment device is moved from the first sheath to the second sheath across the gap, a distal region of the first element expands from the compressed state within the gap while the second element generally maintains its diameter in the compressed state while crossing the gap.
41. The device of Clause 40, wherein the second channel is surrounded by a sidewall having an outer diameter, and wherein the distal region of the first element expands over the outer diameter of the sidewall as it crosses the gap.
42. The device of Clause 40 or Clause 41, wherein an inner diameter of the second channel tapers distally from the second proximal opening.
43. The device of any one of Clauses 40-42, wherein the second channel is surrounded by a sidewall having an outer diameter that increases distally from the second proximal opening.

44. The device of any one of Clauses 40-43, wherein the first and second channels are fixed relative to one another.

45. The device of any one of Clauses 40-44, wherein the first and second channels are movable relative to one another.

46. The device of any one of Clauses 40-45, wherein the length is a first length, and wherein the device is configured to securely position the first and second channels relative to one another such that the gap has a second length greater than the first length.

47. A sheathing tool, comprising:
   a support;
   a loading member coupled to the support and having a first distal opening, a first proximal opening, and a first channel extending therebetween, wherein the first proximal opening is configured to receive a first sheath therethrough; and
   a receiving member coupled to the support and having a second distal opening, a second proximal opening, and a second channel extending therebetween, wherein the second distal opening is configured to receive a second sheath therethrough,
   wherein the support is configured to securely position the loading member and the receiving member relative to one another such that the first distal opening is aligned with the second proximal opening and spaced apart from the second proximal opening by a gap, the gap having a length such that, when the first and second sheaths are positioned within the first and second channels, respectively, and a self-expanding treatment device is moved in a compressed state from a lumen of the first sheath to a lumen of the second sheath across the gap, a distal portion of the treatment device maintains its diameter in the compressed state between the first distal opening and the second proximal opening.

Additional features and advantages of the subject technology are described below, and in part will be apparent from the description, or may be learned by practice of the subject technology. The advantages of the subject technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIGS. 4A-4H illustrate a method of using a sheathing tool to sheath a treatment device.

FIG. 8A is an isometric view of a sheathing tool in a first position configured in accordance with the present technology.

FIG. 8B is a side cross-sectional view of the sheathing tool of FIG. 8A in a second position configured in accordance with the present technology.

FIG. 8C is an isometric view of the connector of the sheathing tool shown in FIGS. 8A and 8B.

DETAILED DESCRIPTION

The present technology provides devices, systems, and methods for sheathing and/or re-sheathing an intravascularly deliverable treatment device. Although many of the embodiments are described below with respect to devices, systems, and methods for removing clot material/treating embolism (such as a cerebral embolism), the sheathing tools of the present technology may be used to re-sheath any intravascularly deliverable, expandable treatment device. Other applications and other embodiments in addition to those described herein are within the scope of the technology. For example, the sheathing tools of the present technology may be used with devices for removing emboli from body lumens other than blood vessels (e.g., the digestive tract, etc.) and/or may be used to remove emboli from blood vessels outside of the brain (e.g., pulmonary blood vessels, blood vessels within the legs, etc.). In addition, the sheathing tools of the present technology may be used with devices for removing luminal obstructions other than clot material (e.g., plaque, resected tissue, etc.).

1. System Overview

Figure 1:
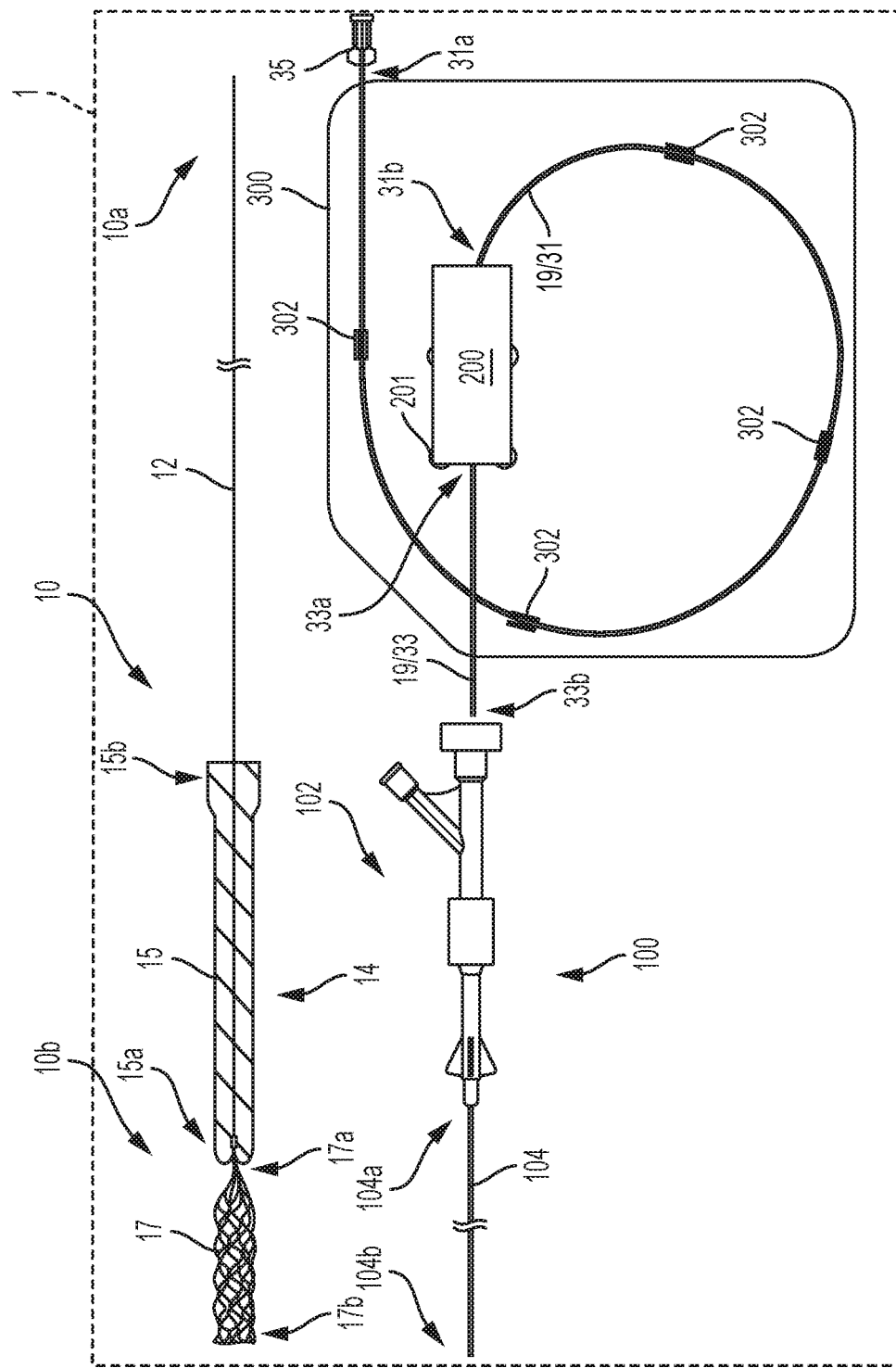
FIG. 1 is a schematic overview of a treatment system configured in accordance with the present technology.

FIG. 1 is a schematic representation of a system 1 ("system 1") configured in accordance with the present technology. As shown in FIG. 1, the system 1 may include a treatment device 10 (shown in an expanded, unconstrained state), a catheter 100 (e.g., a microcatheter), a sheathing tool 200 (shown schematically), a support 300, and a sheath 19 for facilitating introduction of the treatment device 10 to the catheter 100 and/or sheathing tool 200. The catheter 100 may include a handle 102 and an elongated shaft 104 having a proximal portion 104a coupled to the handle 102 and a distal portion 104b configured to be positioned at a treatment site within a blood vessel lumen (e.g., a cerebral blood vessel lumen). The elongated shaft 104 is configured to slidably receive the treatment device 10 in a low-profile, constrained state (not shown) therethrough.

The sheath 19 may be configured to be detachably coupled to the catheter 100, the sheathing tool 200, and/or the support 300 and is configured to slidably receive the treatment device 10 in a low-profile, constrained state (not shown) therethrough. In some embodiments, such as the embodiment shown in FIG. 1, the sheath 19 may include a first segment 31 and a second segment 33. The first segment 31 may have a proximal portion 31a and a distal portion 31b configured to be detachably coupled to the sheathing tool 200, and the second segment 33 may have a proximal portion 33a configured to be detachably coupled to the sheathing tool 200 and a distal portion 33b configured to be detachably coupled to the handle 108 of the catheter 100, thereby creating a pathway between the lumen of the second segment and the lumen of the elongated shaft 104.

As shown in FIG. 1, the sheathing tool 200 and/or one or more portions of the sheath 19 may be configured to be detachably or permanently coupled to the support 300. For example, to secure the sheathing tool 200 and/or the sheath 19 to the support 300, the support 300 may include one or more tabs, slots, protrusions or other means 302 for engaging the sheath 19 and/or the sheathing tool 200 and/or one or more corresponding tabs, protrusions, slots, etc. on the sheath 19 and/or the sheathing tool 200. In some embodiments, the system 1 may be packaged with one or both of the sheathing tool 200 and the sheath 31 detachably or permanently mounted on the support 300.

In some embodiments, the treatment device 10 includes an elongated member 12 and a treatment assembly 14 coupled to a distal region of the elongated member 12. The treatment assembly 14 may be configured to be intravascularly positioned at or adjacent clot material within a blood vessel lumen and includes a first element 17 and a second element 15. In some embodiments, the first element 17 may be a self-expanding stent 17 (e.g., a laser-cut stent) and the second element 15 may be a self-expanding mesh (e.g., a braid, a weave, a lattice structure, a fabric, etc.). In some embodiments, the first and second elements 17, 15 may have other suitable configurations.

Figure 2:
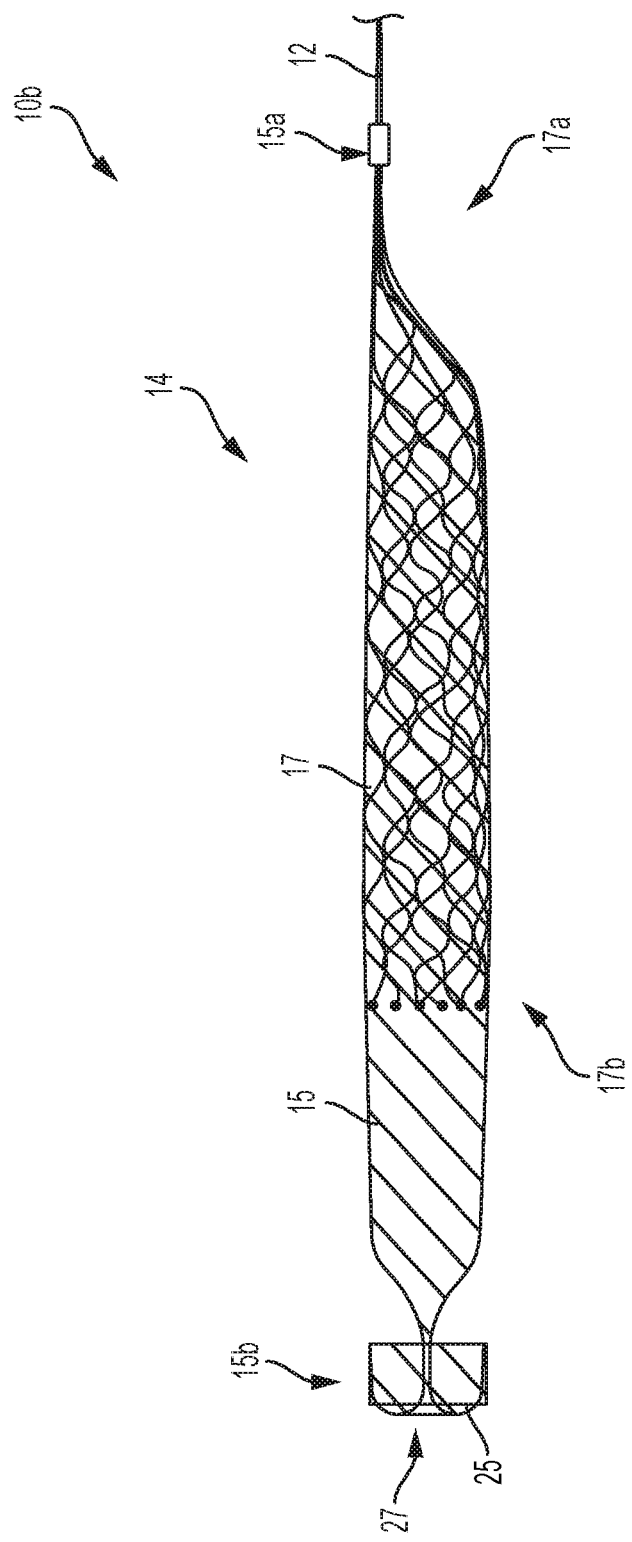
FIG. 2 is a side view of a distal portion of the treatment device shown in FIG. 1 in a second position in accordance with embodiments of the present technology.

The first element 17 may have a proximal portion 17a coupled to the elongated member 12 and a distal portion 17b, and the second element 15 may have a free end portion 15b and a fixed end portion 15a coupled to the elongated member 12. The second element 15 may be flexible such that it is movable between a first position (FIG. 1) in which its free end portion 15b is proximal of its fixed end portion 15a, and a second position (see FIG. 2) in which the second element 15 is inverted over the first element 17 such that a distal terminus of the second element 15 is at or distal to the distal terminus of the first element 17. As shown in FIG. 2, when the second element 15 is in the second position, the free end portion 15b is distal of the fixed end portion 15a and distal of the distal terminus of the first element 17. In the second position, the second element 15 may have a flared distal region 25 that surround a lumen 27 therethrough.

Examples of suitable treatment devices 10 for use with the system 1 can be found in U.S. patent application Ser. No. 15/594,410, filed May 12, 2017, which is incorporated by reference herein in its entirety. Although the sheathing tools discussed below are described with reference to the treatment device 10 shown in FIGS. 1 and 2, the sheathing tools disclosed herein may be utilized to sheath or re-sheath any expandable treatment device deliverable through a catheter.

2. Selected Embodiments of Sheathing Tools and Associated Methods of Use

Figure 3A:
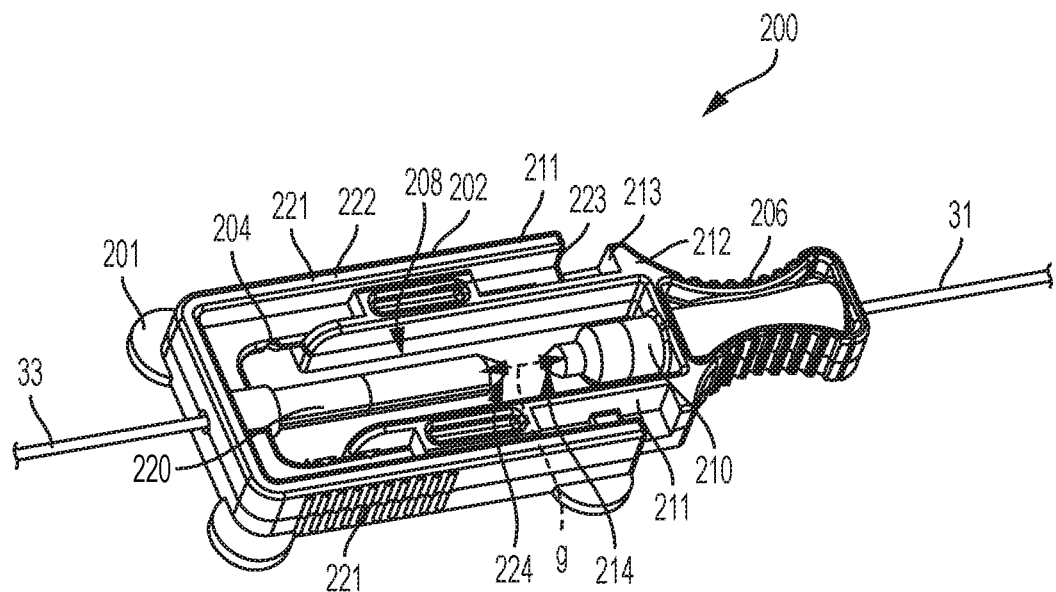
FIG. 3A is an isometric view of a sheathing tool in a first position configured in accordance with the present technology.
Figure 3B:
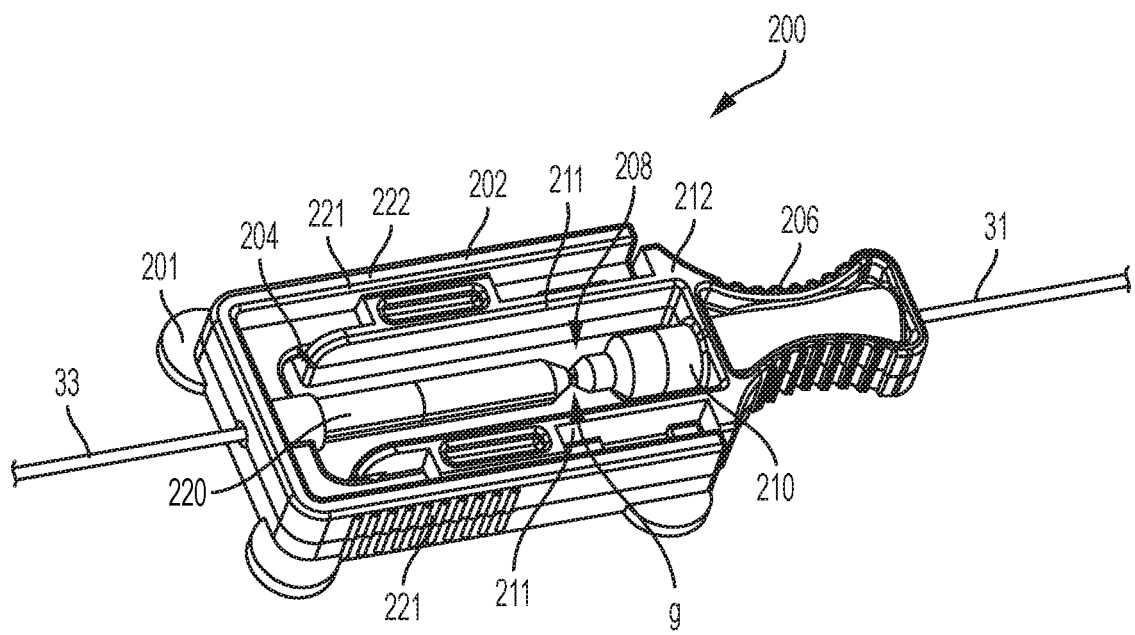
FIG. 3B is an isometric view of the sheathing tool of FIG. 3A in a second position configured in accordance with the present technology.
Figure 3C:
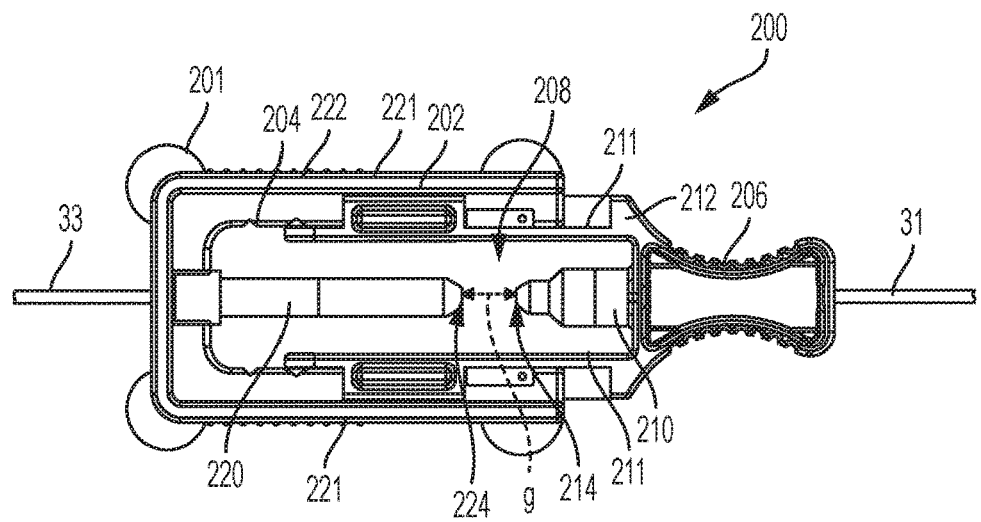
FIG. 3C is a top view of the sheathing tool in the first position, as shown in FIG. 3A.
Figure 3F:
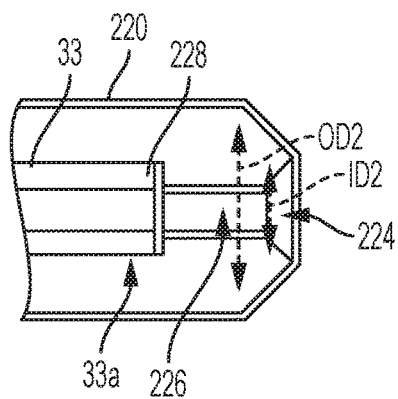
FIG. 3F is an enlarged, isolated view, cross-sectional view of the second channel shown in FIGS. 3A-3D.

FIGS. 3A and 3C are an isometric view and a top view of a sheathing tool 200, respectively, in a first position configured in accordance with embodiments of the present technology. FIGS. 3B and 3D are an isometric view and a top view of the sheathing tool 200, respectively, in a second position configured in accordance with embodiments of the present technology. Referring to FIGS. 3A-3D together, the sheathing tool 200 may include a housing 202 having a first portion 212 and a second portion 222 slidably coupled to the first portion 212. The first portion 212 may include a first protrusion 210 and first arms 211 extending distally beyond the first protrusion 210, and the second portion 222 may include a second protrusion 220 and second arms 221 extending proximally beyond the second protrusion 220. The first and second arms 211, 221 can be coupled along at least a portion of their lengths and together surround an open interior region 208 of the housing 202 into which the first and second protrusions 210, 220 extend. As such, the first and second protrusions 210, 220 are spaced apart from the adjacent first and second arms 211, 221. In some embodiments, the first protrusion 210 is not spaced apart from the adjacent first arms 211.

Figure 3E:
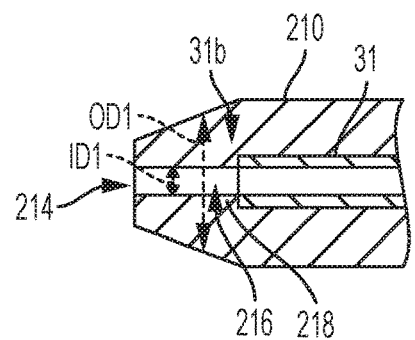
FIG. 3E is an enlarged, isolated, cross-sectional view of the first channel shown in FIGS. 3A-3D.
Figure 3D:
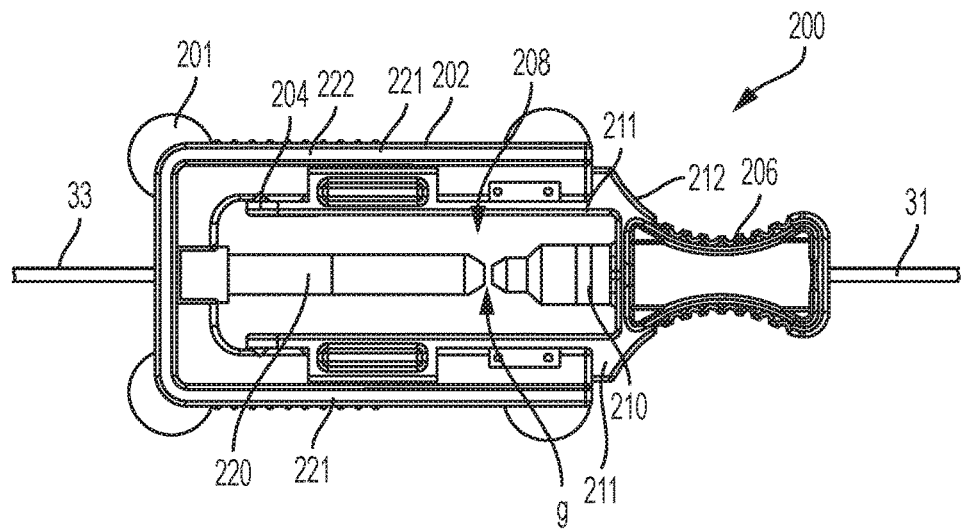
FIG. 3D is a top view of the sheathing tool in the second position, as shown in FIG. 3B.

FIG. 3E is an enlarged, isolated, cross-sectional view of a distal region of the first protrusion 210. As shown in FIG. 3E, the first protrusion 210 may include a first channel 216 extending distally from a proximal region of the proximal portion 212 of the housing 202 to a first opening 214. In some embodiments the first channel 216 may be configured to receive the treatment device 10 in a constrained state therethrough, and in some embodiments the first channel 216 may be configured to receive the sheath 19. In FIG. 3E, for example, the first sheath segment 31 is shown positioned within the first channel 216. The first channel 216 may be surrounded by a generally tubular sidewall having an outer diameter OD1 that tapers in a distal direction. An inner diameter ID1 of the first channel 216 may taper distally to help guide the first element 17 in a generally constrained state towards the second opening 224.

FIG. 3F is an enlarged, isolated, cross-sectional view of a proximal region of the second protrusion 220. As shown in FIG. 3E, the second protrusion 220 may include a second channel 226 extending proximally from a distal region of the distal portion 222 of the housing 202 to a second opening 224. In some embodiments the second channel 226 may be configured to receive the treatment device 10 in a constrained state therethrough, and in some embodiments the second channel 226 may be configured to receive the sheath 19. In FIG. 3F, for example, the second sheath segment 33 is shown positioned within the second channel 226. The second channel 226 may be surrounded by a generally tubular sidewall having an outer diameter OD2 that tapers in a proximal direction to facilitate positioning the second element 15 over the second protrusion 220. In some embodiments, an inner diameter ID2 of the second channel 216 may taper distally to help guide and/or deflect the first element 17 into the second channel 226 and/or the second sheath segment 33.

When the sheathing tool 200 is in a first position, the first and second openings 214, 224 are spaced apart by a gap g having a first length, and when the sheathing tool 200 is in a second position, the first and second openings 214, 224 are spaced apart by a gap g having a second length less than the first length. The second length may be great enough to allow the second element 15 to self-expand such that the second element 15 is positioned over the sidewall while the first element 17 generally maintains its diameter in the constrained state while crossing the gap g. In other words, because the first element 17 does not have enough space between the first and second openings 214, 224 to expand, the first element 17 crosses the gap g in a constrained state which allows the first element 17 to enter through the second opening 224. If the gap g is too long, the distal ends of the first element 17 may begin to expand/splay outwardly and prevent the first element 17 from entering the second channel 226. Likewise, if the gap g is too short, the second element 15 may not have enough room for the distal portion 15b to flare radially outwardly to an extent that allows the second element 15 to extend over the second protrusion 222 and/or receive the second protrusion 222 within the lumen 27 (FIG. 2) of the distal region 15b.

Figure 4C:
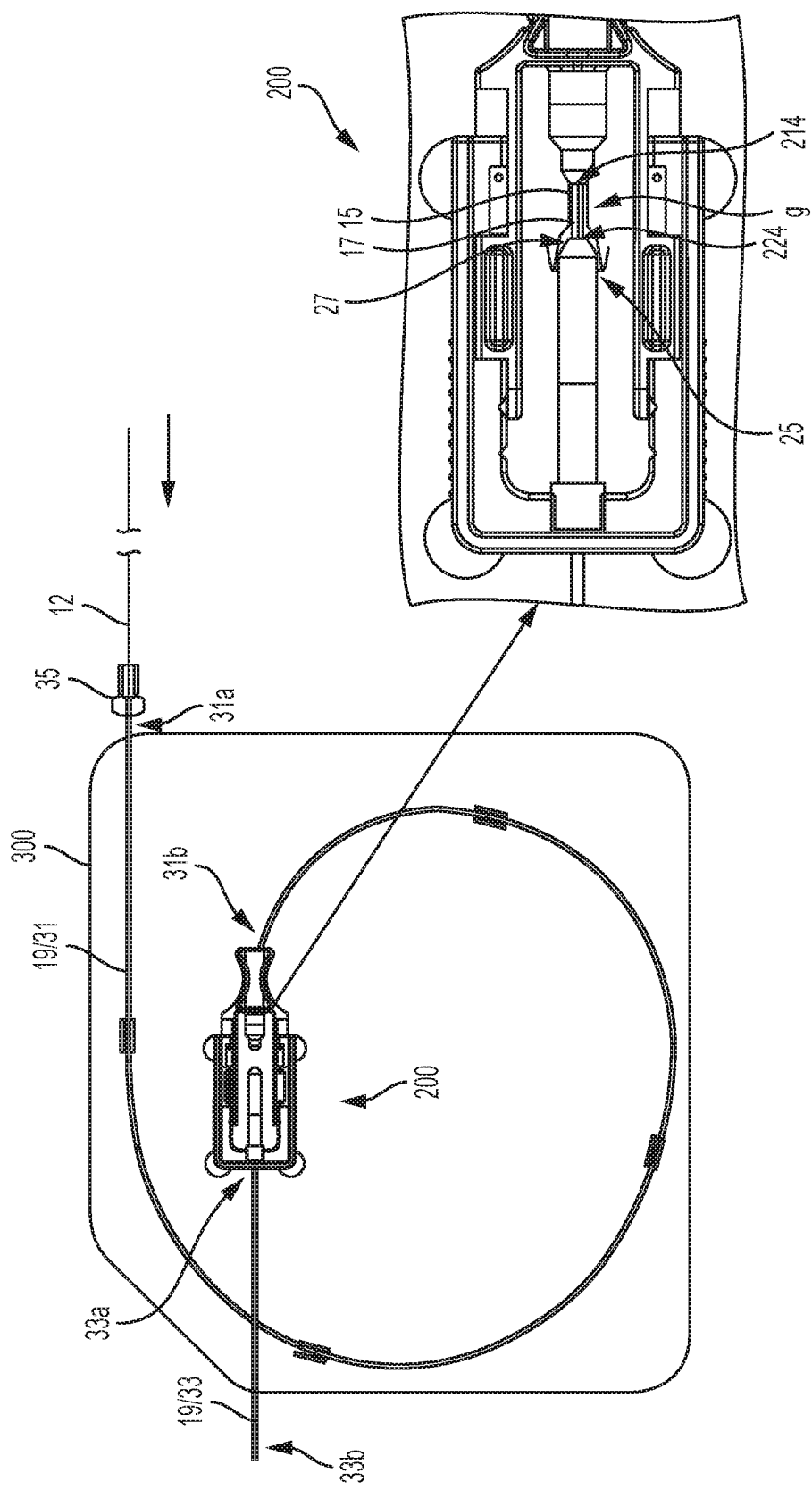

FIGS. 4A-4H illustrate a method of using the sheathing tool 200 to sheath and/or re-sheath the treatment device 10. As shown in FIG. 4A, in some embodiments the treatment device 10 may first be withdrawn proximally from a treatment site through the blood vessel V lumen and catheter 100. Once removed from the catheter 100, the treatment device 10 may be in an expanded, unconstrained state in the second position such that the second element 15 is inverted over the first element 17. As shown in FIG. 4B, the treatment device 10 in the second position may then be pulled proximally through the second sheath segment 33, then the sheathing tool 200, and into the first sheath segment 31. For example, a proximal end of the elongated member 12 may be inserted into an opening at the distal portion 33b of the second segment 33, and the rest of the elongated member 12 may be pushed proximally through the second sheath segment 33, the sheathing tool 200, and at least a portion of the first sheath segment 31 (and/or pulled once the proximal end of the elongated member 12 exits a proximal portion 31a of the first sheath segment 31). Once a distal portion of the treatment device 10 is aligned with or proximal of the first opening 214, the elongated member 12 may then be pushed distally, thereby advancing the first and second elements 17, 15 across the gap g, as shown in FIG. 4C. While moving the treatment device 10 across the gap, the first element 17 may maintain its cross-sectional dimension in the constrained state while the second element 15 expands over the sidewall surrounding the second opening 224. (In FIG. 4C, the first and second elements 17, 15 are shown in cross-section for ease of viewing the treatment device 10 within the gap g.) In some embodiments, the first element 17 may be advanced across the gap g and into the second opening 224 while the sheathing tool 200 is in the first position. In some embodiments, the first element 17 may only be advanced across a portion of the gap g (and not into the second opening 224) while the sheathing tool 200 remains in the first position.

Figure 4D:
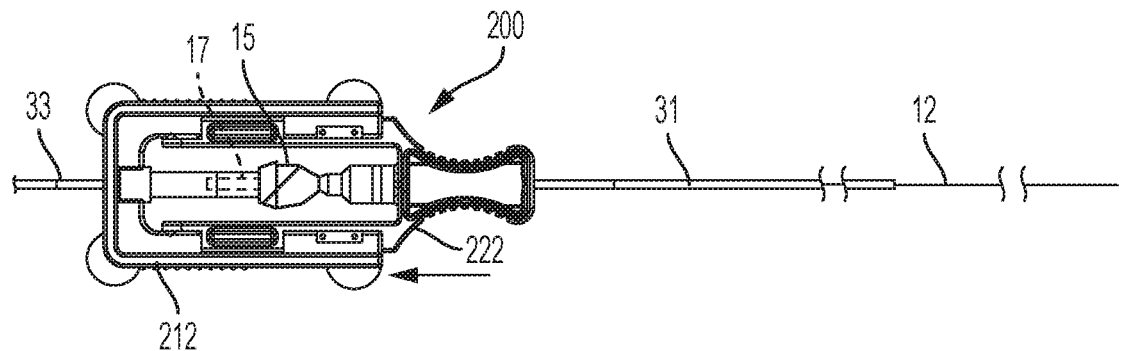
Figure 4E:
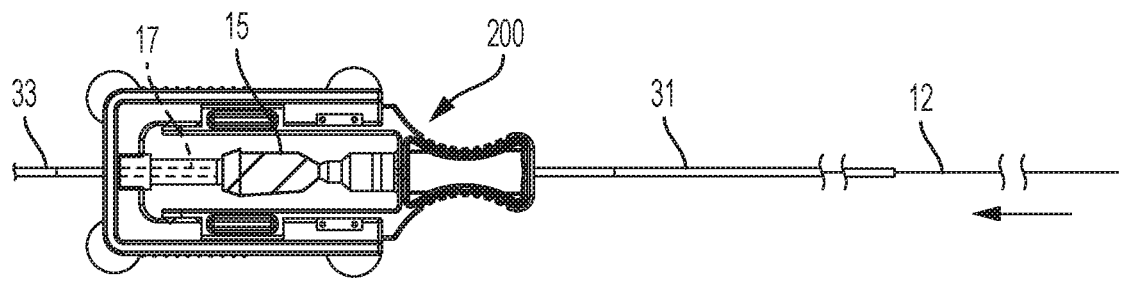
Figure 4F:
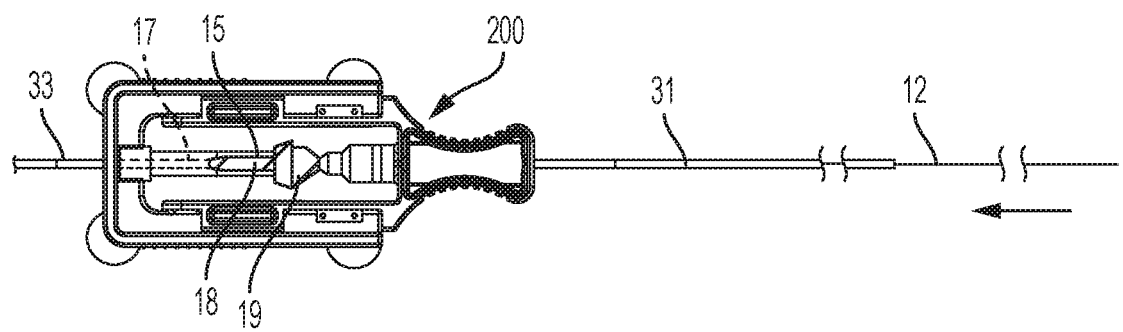
Figure 4G:
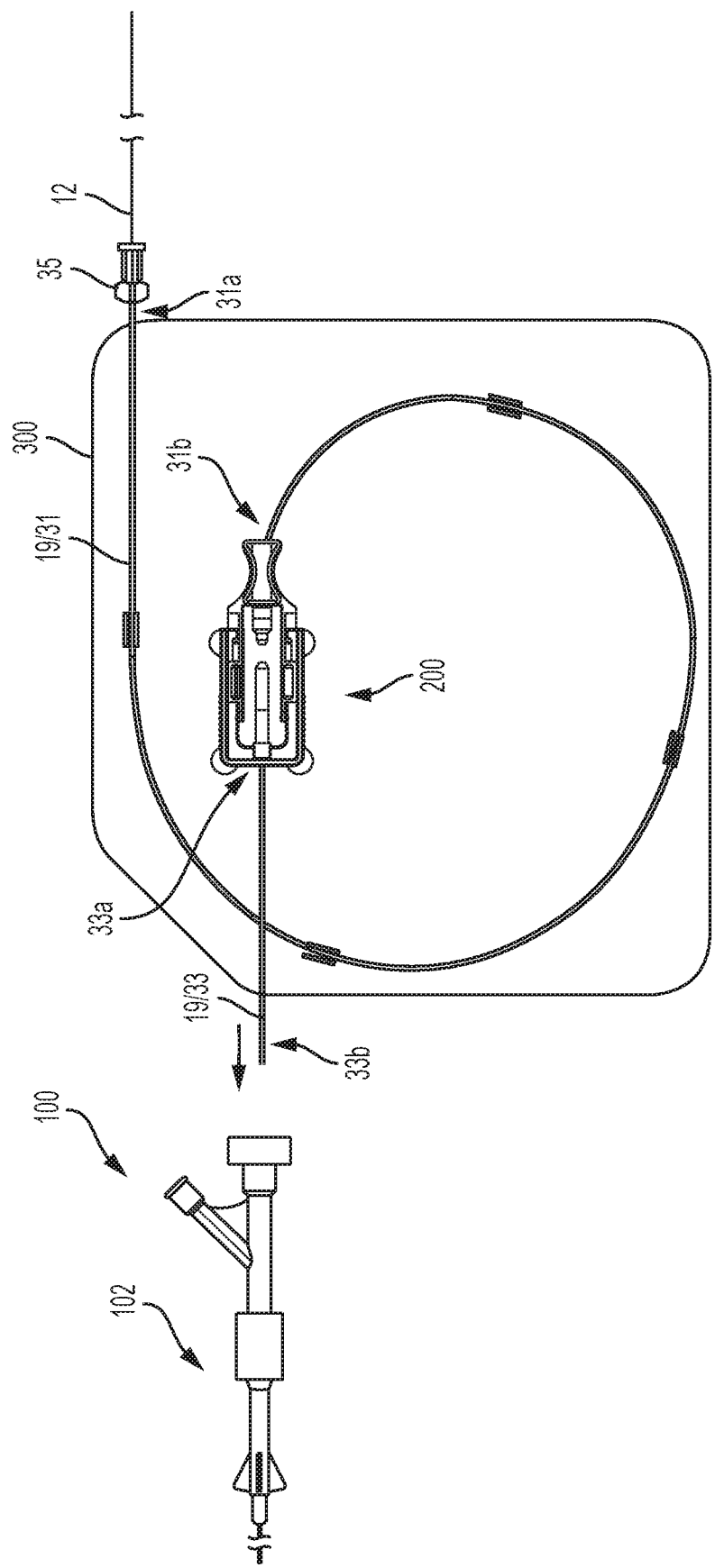
Figure 4H:
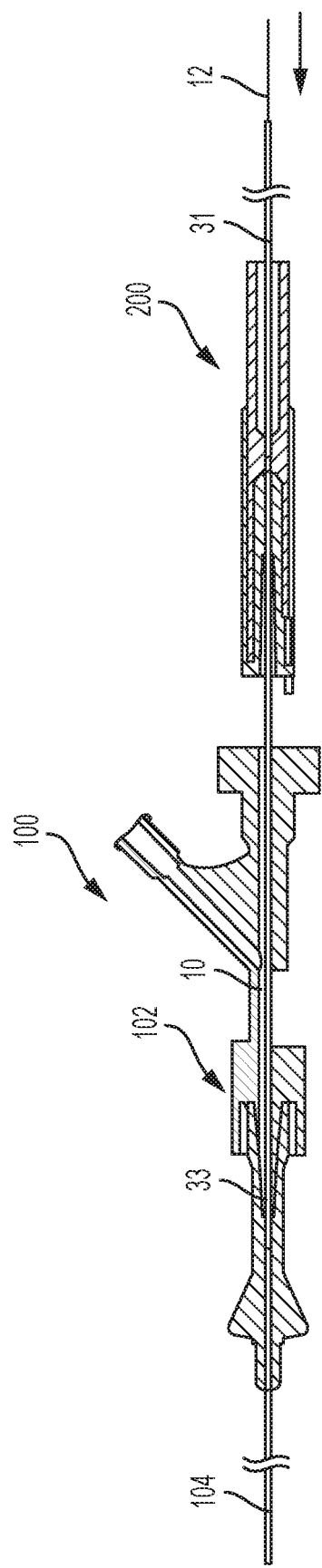

As shown in FIG. 4D, the first portion 212 of the housing 202 may be moved towards the second portion 222 of the housing 202 and secured in place by one or more detents and/or other securement features of the housing 202. Moving the first and second openings towards one another forces the second protrusion 220 further within the lumen of the second element 15. As shown in FIGS. 4E and 4F, the elongated member 12 can be pushed proximally while the sheathing tool 200 is in the second position, thereby advancing the first element 17 further within the second channel 126 and/or second sheath segment 33. As the elongated member 12 is advanced distally, the second element 15 extends further distally along the second protrusion 220 until it's fixed end portion pulls the second element 15 into the second channel 226. As such, a portion of the second element may move in a first direction through the second channel while a second portion of the second element moves in a second direction opposite the first direction outside of the second channel 226. As shown in FIG. 4G, the second sheath segment 33 may then be coupled to the catheter 100. As shown in FIG. 4H, the elongated member 12 may be pushed proximally to transfer the treatment device 10 in the first position from the second sheath segment 33 to the catheter 100.

Figure 5B:
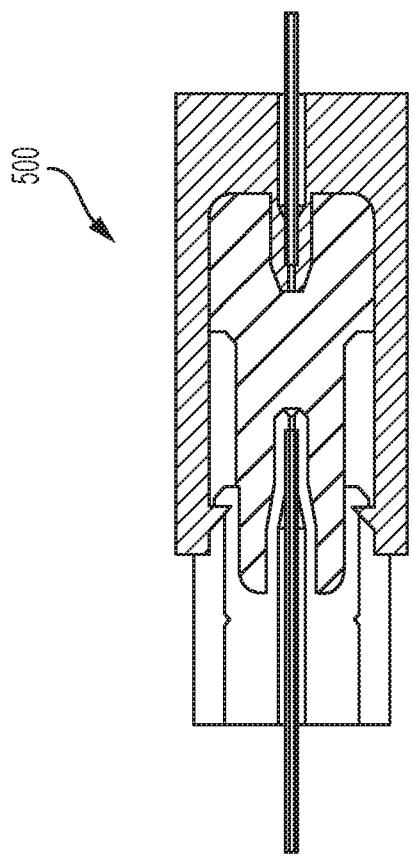
FIGS. 5A and 5B are an isometric view and a top cross-sectional view, respectively, of a sheathing tool shown in a first position configured in accordance with some embodiments of the present technology.
Figure 5D:
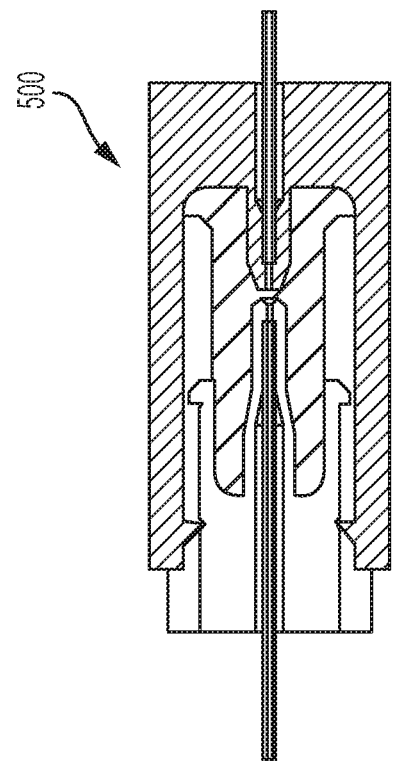
FIGS. 5C and 5D are an isometric view and a top cross-sectional view, respectively, of the sheathing tool shown in FIGS. 5A and 5B in a second position configured in accordance with some embodiments of the present technology.
Figure 5A:
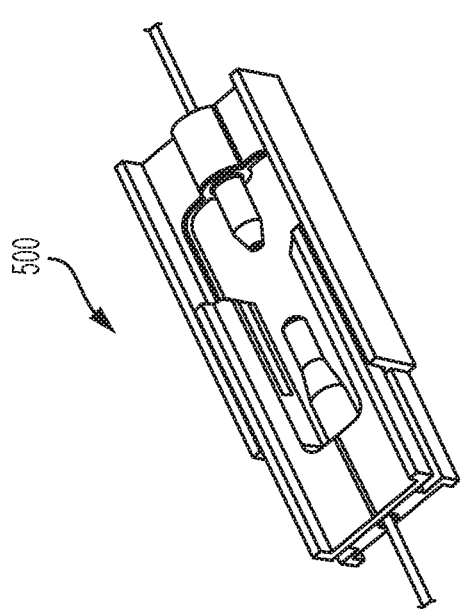
Figure 5C:
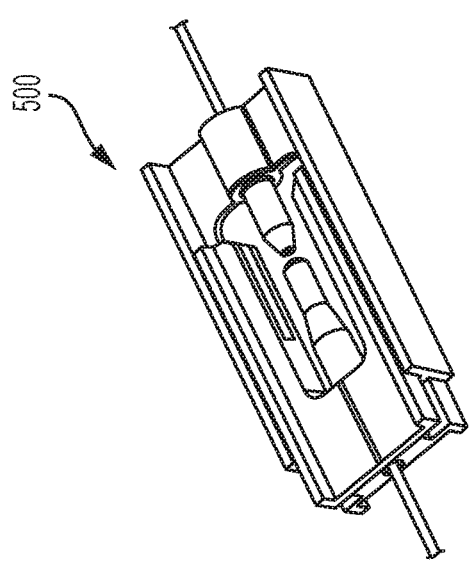

FIGS. 5A and 5B are an isometric view and a top cross-sectional view, respectively, of a sheathing tool shown in a first position configured in accordance with some embodiments of the present technology. FIGS. 5C and 5D are an isometric view and a top cross-sectional view, respectively, of the sheathing tool shown in FIGS. 5A and 5B in a second position configured in accordance with some embodiments of the present technology.

Figure 6A:
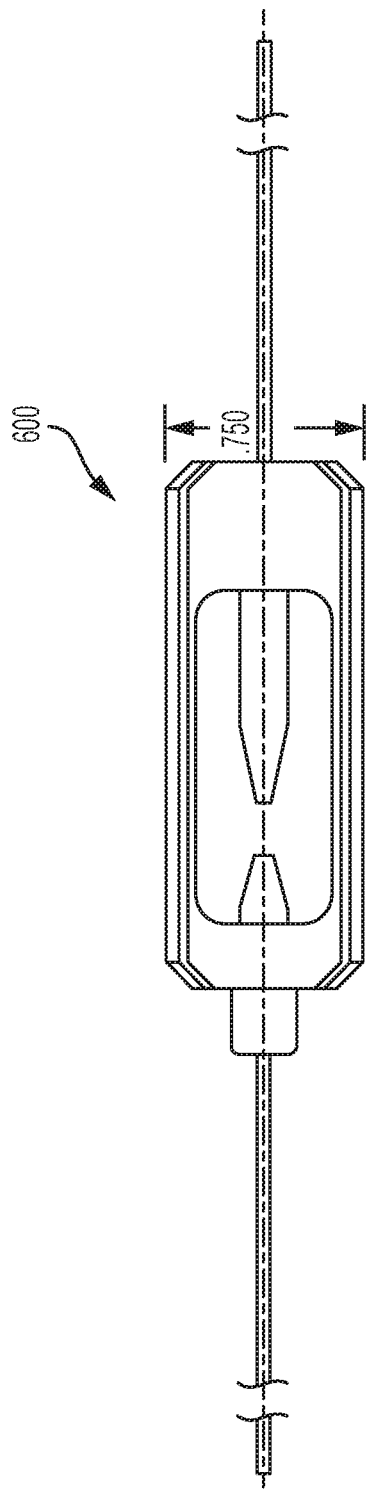
FIGS. 6A and 6B are a top view and a side cross-sectional view, respectively, of a sheathing tool shown in a first position configured in accordance with some embodiments of the present technology.
Figure 6B:
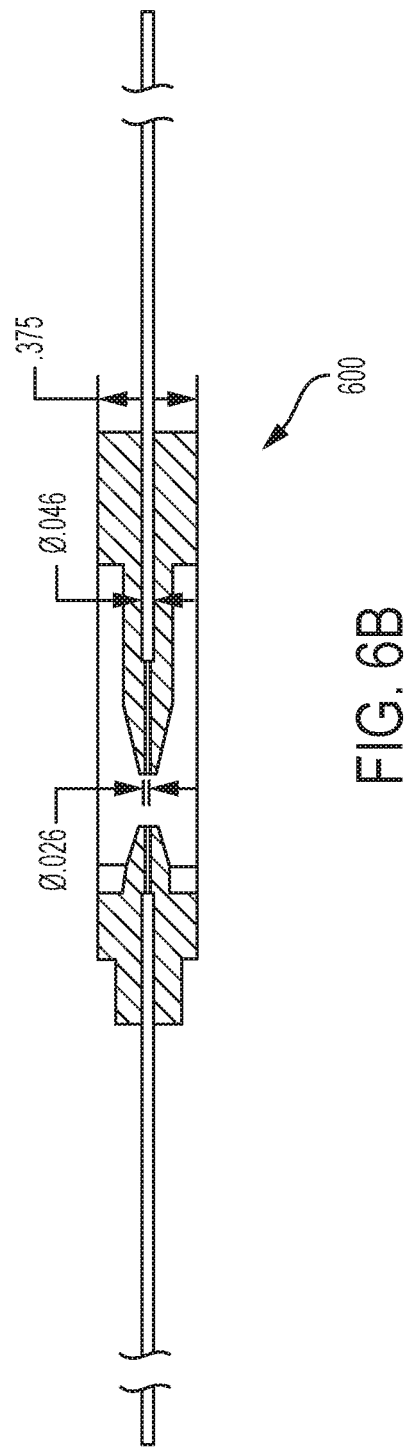

FIGS. 6A and 6B are a top view and a side cross-sectional view, respectively, of a sheathing tool 600 shown in a first position configured in accordance with some embodiments of the present technology. In some embodiments, such as that shown in FIGS. 6A and 6B, the housing 202 may be a single component and/or the first and second openings are spaced apart by a fixed distance.

Figure 7B:
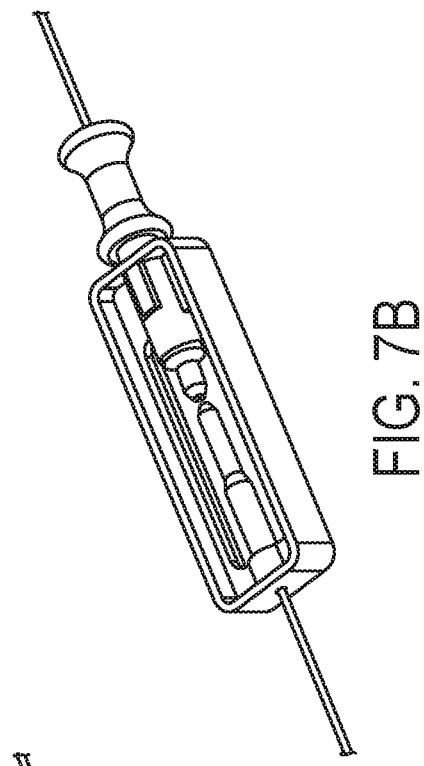
FIG. 7B is an isometric view of the sheathing tool of FIG. 7A in a second position configured in accordance with the present technology.
Figure 7A:
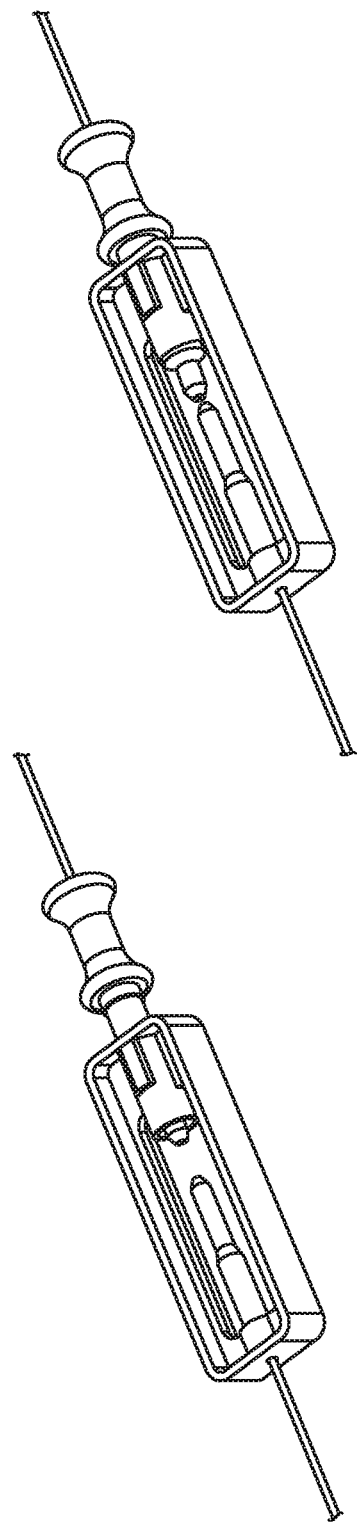
FIG. 7A is an isometric view of a sheathing tool in a first position configured in accordance with the present technology.
Figure 7C:
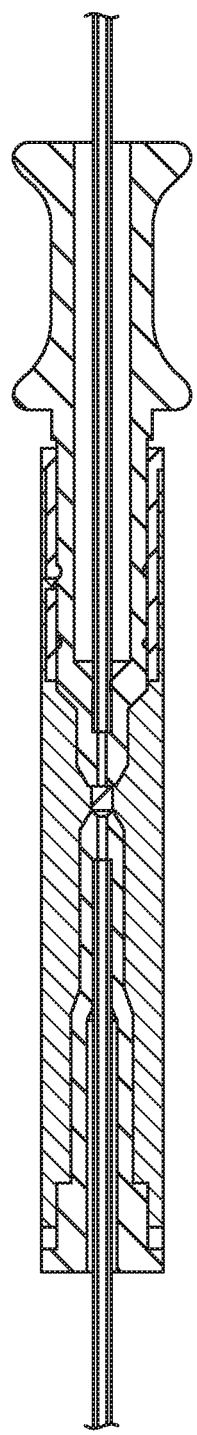
FIG. 7C is a side cross-sectional view of the sheathing tool as shown in FIG. 7B.
Figure 7D:
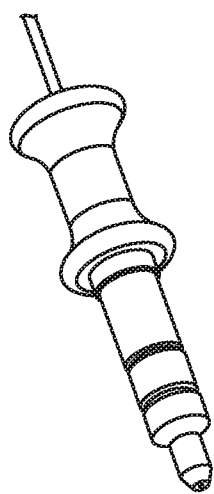
FIG. 7D is an isometric view of the connector of the sheathing tool shown in FIGS. 7A-7C.

FIG. 7A is an isometric view of a sheathing tool in a first position configured in accordance with the present technology. FIG. 7B is an isometric view of the sheathing tool of FIG. 7A in a second position configured in accordance with the present technology FIG. 7C is a side cross-sectional view of the sheathing tool as shown in FIG. 7B. FIG. 7D is an isometric view of the connector of the sheathing tool shown in FIGS. 7A-7C.

FIG. 8A is an isometric view of a sheathing tool in a first position configured in accordance with the present technology. FIG. 8B is a side cross-sectional view of the sheathing tool of FIG. 8A in a second position configured in accordance with the present technology. FIG. 8C is an isometric view of the connector of the sheathing tool shown in FIGS. 8A and 8B.

Figure 9A:
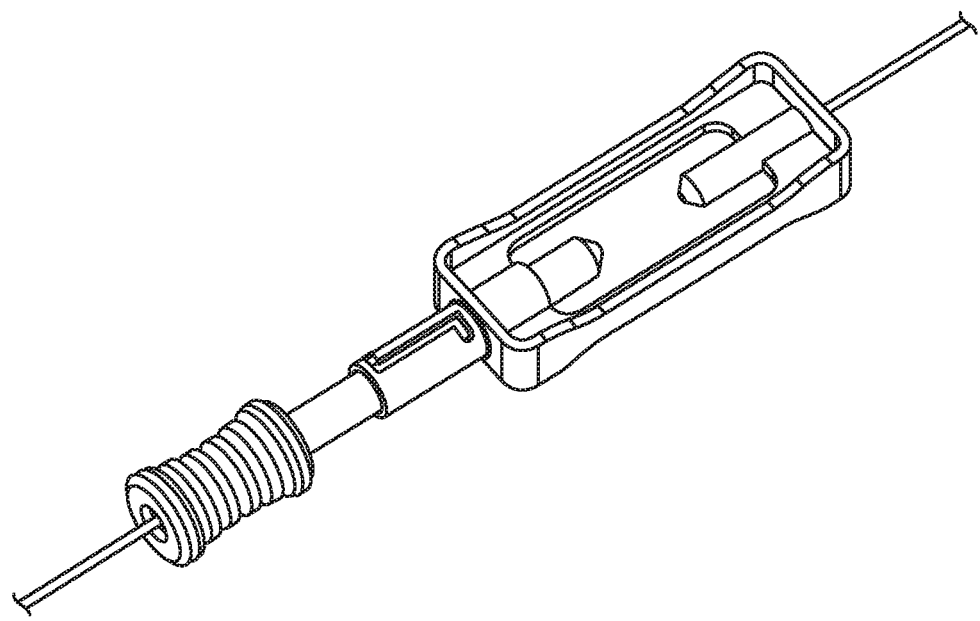
FIG. 9A is an isometric view of a sheathing tool in a first position configured in accordance with the present technology.
Figure 9B:
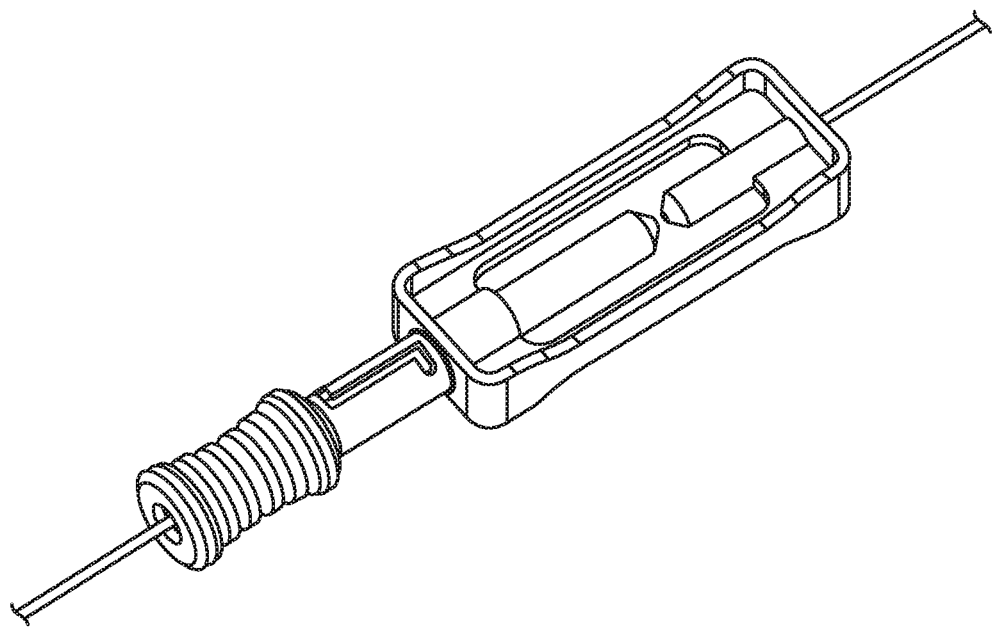
FIG. 9B is an isometric view of the sheathing tool of FIG. 7A in a second position configured in accordance with the present technology.

FIG. 9A is an isometric view of a sheathing tool in a first position configured in accordance with the present technology. FIG. 9B is an isometric view of the sheathing tool of FIG. 7A in a second position configured in accordance with the present technology.

3. Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A system comprising: a treatment device having an elongated member, and a first element and a second element at a distal region of the elongate member; and a device for sheathing the treatment device, the device comprising: a first channel extending to a first opening, the first channel configured to receive the treatment device in a constrained state therethrough; and a second channel extending to a second opening, the second opening surrounded by a sidewall and configured to receive the treatment device in the constrained state therethrough, wherein the second opening is spaced apart from the first opening by a gap, and wherein a length of the gap is great enough to allow the first element to self-expand over the sidewall while the second element generally maintains its diameter in the constrained state while crossing the gap.

2. The system of claim 1, wherein an inner diameter of the second channel tapers distally from the second opening.

3. The system of claim 1, wherein an outer diameter of the sidewall increases distally from the second opening.

4. The system of claim 1, wherein the first and second openings are fixed relative to one another such that the length of the gap is fixed.

5. The system of claim 1, wherein the first and second openings are movable relative to one another such that the length of the gap is adjustable.

6. The system of claim 1, wherein the first channel is within a first housing and the second channel is within a second housing movable relative to the first housing, and wherein the first housing has a detent configured to receive a protrusion of the second housing, or vice versa, such that the first housing is locked in place relative to the second housing.

7. The system of claim 1, wherein the first channel is configured to receive a sheath therethrough, wherein the sheath is configured to slidably receive the treatment device therein in the constrained state.

8. The system of claim 1, wherein the second channel is configured to receive a sheath therethrough, and wherein the sheath is configured to slidably receive the treatment device therein in the constrained state.

9. The system of claim 1, wherein the first element is a self-expanding element.

10. The system of claim 1, wherein the second element is a self-expanding element.

11. The system of claim 1, wherein the first element is a mesh.

12. The system of claim 1, wherein the second element is a stent.

13. The system of claim 1, wherein, in an expanded state, the first element has a flared distal region with a lumen therethrough, and wherein the lumen of the flared distal region is configured to receive the sidewall therein as the treatment device is moved across the gap.

14. The system of claim 1, wherein the treatment device is a clot retrieving device.

15. The system of claim 1, wherein the device is configured to be detachably coupled to a handle of a catheter, thereby placing the second channel in fluid communication with a lumen of the catheter.

* * * * *

UNITED STATES PATENT AND TRADEMARK OFFICE
CERTIFICATE OF CORRECTION

PATENT NO. : 10,945,746 B2
APPLICATION NO. : 16/007961
DATED : March 16, 2021
INVENTOR(S) : Epstein et al.

Page 1 of 1

It is certified that error appears in the above-identified patent and that said Letters Patent is hereby corrected as shown below:

In the Claims

In Column 13, in Claim 1, Line 44, delete "elongate" and insert -- elongated --, therefor.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*